US009814622B2

(12) United States Patent
Sommers

(10) Patent No.: US 9,814,622 B2
(45) Date of Patent: Nov. 14, 2017

(54) BUMP CAP FOR FACE PROTECTION MEMBERS

(71) Applicant: Illinois Tool Works Inc., Glenview, IL (US)

(72) Inventor: Eric Sommers, Appleton, WI (US)

(73) Assignee: ILLINOIS TOOL WORKS INC., Glenview, IL (US)

(*) Notice: Subject to any disclaimer, the term of this patent is extended or adjusted under 35 U.S.C. 154(b) by 0 days.

(21) Appl. No.: 14/738,206

(22) Filed: Jun. 12, 2015

(65) Prior Publication Data

US 2016/0361201 A1 Dec. 15, 2016

(51) Int. Cl.
*A61F 9/06* (2006.01)
*A42B 3/06* (2006.01)
*A42B 3/22* (2006.01)

(52) U.S. Cl.
CPC .................. *A61F 9/06* (2013.01); *A42B 3/06* (2013.01); *A42B 3/225* (2013.01)

(58) Field of Classification Search
CPC .. A61F 9/06; A61F 9/061; A61F 9/062; A61F 9/064; A61F 9/065; A61F 9/067; A61F 9/068; A42B 3/225
USPC ....... 2/8.1, 8.2, 8.3, 8.5, 8.6, 9, 10, 15, 421, 2/422, 424
See application file for complete search history.

(56) References Cited

U.S. PATENT DOCUMENTS

| | | | |
|---|---|---|---|
| 1,182,367 A | 5/1916 | Gravell | |
| 1,338,022 A | 4/1920 | Lamoreaux | |
| 1,601,830 A | 10/1926 | Huntsman | |
| 1,947,786 A * | 2/1934 | Lueck | A42B 3/225 2/10 |
| 1,994,103 A | 3/1935 | Huey | |
| 2,169,745 A | 8/1939 | Shipman | |
| 2,194,492 A | 3/1940 | Bowers | |
| 2,358,978 A * | 9/1944 | Huntsman | A42B 3/225 2/8.1 |
| 2,411,831 A | 11/1946 | Lehmberg et al. | |
| 2,487,848 A | 11/1949 | Bowers | |
| 2,658,200 A | 11/1953 | Bowers, Sr. | |
| 2,700,158 A | 1/1955 | Larsen | |
| 2,763,006 A | 9/1956 | Amundsen | |
| 3,074,072 A | 1/1963 | Edwards et al. | |
| 3,214,768 A | 11/1965 | Bohner | |
| 3,380,073 A * | 4/1968 | McLaughlin | A61F 9/06 2/10 |

(Continued)

FOREIGN PATENT DOCUMENTS

AU 2010 100 565 A4 7/2010
EP 1136007 A2 9/2001
(Continued)

OTHER PUBLICATIONS

International Search Report and Written Opinion for PCT/US2015/065213 dated Mar. 16, 2016, 13 pages.
(Continued)

*Primary Examiner* — Katherine Moran
(74) *Attorney, Agent, or Firm* — Klintworth & Rozenblat IP LLP

(57) ABSTRACT

A system is disclosed for attaching a bump cap to a welding headgear. The system includes a bump cap, and an attachment member. The attachment member is configured to attach the bump cap to a welding headgear.

11 Claims, 6 Drawing Sheets

(56) References Cited

U.S. PATENT DOCUMENTS

| | | |
|---|---|---|
| 3,430,263 A | 3/1969 | Newcomb |
| 3,609,765 A | 10/1971 | Molitoris |
| 3,696,442 A | 10/1972 | Amundsen |
| 3,781,915 A | 1/1974 | Menold et al. |
| 3,868,727 A | 3/1975 | Paschall |
| 3,881,478 A | 5/1975 | Rosendahl |
| 4,040,123 A | 8/1977 | Williams |
| 4,109,320 A | 8/1978 | Anderson |
| 4,117,554 A | 10/1978 | Palumbo |
| 4,293,757 A | 10/1981 | Niemi |
| D270,642 S | 9/1983 | Watts |
| 4,479,738 A | 10/1984 | Kubnick |
| 4,499,630 A | 2/1985 | Harris |
| 4,686,712 A | 8/1987 | Spiva |
| 4,764,989 A | 8/1988 | Bourgeois |
| 4,793,001 A | 12/1988 | Accardi |
| 4,853,973 A | 8/1989 | Boochard |
| D316,020 S | 4/1991 | Fushiya |
| 5,003,632 A | 4/1991 | Claude |
| 5,012,528 A | 5/1991 | Pernicka |
| 5,040,528 A | 8/1991 | O'Neill |
| 5,044,019 A | 9/1991 | Shewchenko |
| 5,077,836 A | 1/1992 | Idoff et al. |
| D329,590 S | 9/1992 | Chapman |
| 5,386,592 A | 2/1995 | Checkeroski |
| 5,412,811 A | 5/1995 | Hildenbrand |
| D365,666 S | 12/1995 | Gumpp |
| 5,673,431 A * | 10/1997 | Batty .................. A61F 9/027 2/10 |
| 5,724,119 A | 3/1998 | Leight |
| D393,933 S | 4/1998 | Huh |
| 5,752,280 A | 5/1998 | Hill |
| 5,966,738 A | 10/1999 | Wang Lee |
| D421,116 S | 2/2000 | Mattila |
| 6,032,297 A | 3/2000 | Barthold |
| 6,035,451 A * | 3/2000 | Burns .................. A42B 3/10 2/424 |
| 6,041,435 A | 3/2000 | Paulson et al. |
| 6,055,983 A | 5/2000 | Metzger |
| D433,751 S | 11/2000 | Reischel |
| 6,154,881 A | 12/2000 | Lee |
| 6,260,197 B1 | 7/2001 | Hoogewind |
| 6,264,392 B1 | 7/2001 | Wise |
| D449,103 S | 10/2001 | Legare |
| 6,341,382 B1 | 1/2002 | Ryvin et al. |
| 6,367,085 B1 | 4/2002 | Berg |
| 6,393,617 B1 | 5/2002 | Paris |
| D465,568 S | 11/2002 | Petherbridge |
| D467,489 S | 12/2002 | Rubinson |
| D492,559 S | 7/2004 | Itano |
| 6,782,558 B1 | 8/2004 | Keen, Sr. et al. |
| 6,807,679 B1 | 10/2004 | Wang-Lee |
| 6,892,393 B1 | 5/2005 | Provost et al. |
| 6,973,676 B1 | 12/2005 | Simpson |
| D520,856 S | 5/2006 | Osiecki |
| D520,859 S | 5/2006 | Osiecki |
| D521,190 S | 5/2006 | Wu |
| 7,089,603 B2 | 8/2006 | Ketterer et al. |
| D530,185 S | 10/2006 | Osiecki |
| 7,120,939 B1 | 10/2006 | Howard |
| D543,828 S | 6/2007 | Strutin-Belinoff |
| D557,128 S | 12/2007 | Sawdon |
| 7,441,282 B2 | 10/2008 | Heine |
| D589,654 S | 3/2009 | Juhlin |
| D589,776 S | 4/2009 | Camp |
| D590,232 S | 4/2009 | Demers |
| D600,094 S | 9/2009 | Hwang |
| D617,459 S | 6/2010 | Bogue |
| D626,963 S | 11/2010 | Kim |
| D632,944 S | 2/2011 | Kang |
| 8,214,920 B1 | 7/2012 | Edgar et al. |
| 8,245,320 B2 | 8/2012 | Provost et al. |
| D667,173 S | 9/2012 | Juhlin |
| 8,286,269 B2 | 10/2012 | Springer et al. |
| 8,321,962 B2 | 12/2012 | Moyses |
| 8,336,114 B1 | 12/2012 | Lee |
| D674,150 S | 1/2013 | Juhlin |
| D676,551 S | 2/2013 | Desai |
| 8,381,312 B2 | 2/2013 | Seo |
| D684,252 S | 6/2013 | Okada |
| D687,215 S | 8/2013 | Padgett et al. |
| 8,584,265 B2 | 11/2013 | Lilenthal |
| D696,498 S | 12/2013 | Padgett et al. |
| D710,546 S | 8/2014 | Wu |
| D722,259 S | 2/2015 | Conner |
| 8,990,963 B2 | 3/2015 | Matthews |
| 9,125,448 B2 | 9/2015 | Klotz |
| 9,155,923 B2 | 10/2015 | Proctor |
| 9,427,040 B2 | 8/2016 | Leyland |
| D767,829 S | 9/2016 | Wu |
| 9,516,911 B2 | 12/2016 | Happel |
| 2003/0135911 A1 | 7/2003 | Wang-Lee |
| 2004/0179149 A1 | 9/2004 | Wang-Lee |
| 2006/0080761 A1 | 4/2006 | Huh |
| 2006/0225187 A1 | 10/2006 | Wu |
| 2007/0113318 A1 | 5/2007 | Weston |
| 2007/0220649 A1 * | 9/2007 | Huh .................. A61F 9/025 2/9 |
| 2008/0060102 A1 | 3/2008 | Matthews |
| 2010/0050325 A1 | 3/2010 | Wang-Lee |
| 2010/0229286 A1 | 9/2010 | Ahlgren |
| 2010/0235971 A1 | 9/2010 | Ahlgren |
| 2011/0101890 A1 | 5/2011 | Robinson |
| 2011/0167542 A1 | 7/2011 | Bayne |
| 2012/0084904 A1 | 4/2012 | Paulson |
| 2012/0144565 A1 | 6/2012 | Huh |
| 2014/0298557 A1 | 10/2014 | Townsend, Jr. |
| 2015/0033430 A1 * | 2/2015 | Hofer Kraner .......... A61F 9/06 2/8.2 |
| 2015/0113712 A1 | 4/2015 | Hirschmann, Jr. et al. |
| 2015/0143618 A1 | 5/2015 | Pereira et al. |
| 2016/0081856 A1 | 3/2016 | Hofer-Kraner |
| 2016/0360821 A1 | 12/2016 | Benton |

FOREIGN PATENT DOCUMENTS

| | | |
|---|---|---|
| FR | 2187247 A1 | 1/1974 |
| WO | 2008/025083 A1 | 3/2008 |

OTHER PUBLICATIONS

International Search Report and Written Opinion for PCT/US2816/828219 dated Jul. 6, 2016, 11 pages.

Office action from corresponding Canadian patent Application 2,928,853 dated Feb. 1, 2017, four pages.

European Patent Office English Language Translation of FR2187247, Mussidan Manufacture, Jan. 18, 1974, translated by EPO on Mar. 20, 2017.

Extended European Search Report for Application No. 16169420.3 dated Oct. 21, 2016, 8 pages.

Anonymous: "New optrel weldcap Bump Cap provides additional head protection for welders and metal fabricators", May 15, 2015, pp. 1-2, XP055308892, retrieved from the Internet: URL:http://www.ishn.com/articles/101440-new-optrel-weldcap-bump-cap-provides-additional-head-protection-for-weldeers-and-metal-fabricators.

* cited by examiner

BUMP CAP FOR FACE PROTECTION MEMBERS

FIELD OF THE DISCLOSURE

The disclosure relates to systems and methods for attaching a bump cap to a welding headgear attachable to a face protection member.

BACKGROUND

When head protection is desired during a welding process, such as welding or grinding, to protect the user's head from bumps, there are few viable options. Typical bump caps are not configured to integrate with welding headgear. Hard hat options are typically awkward, inconvenient, and uncomfortable. When a hard hat adapter is utilized, the face protection device sits up much higher on the user's head, thereby throwing off balance and transferring more stress to the user's neck. Other hard hat options are typically heavy and expensive.

A system and method is needed to reduce or eliminate one or more issues of one or more of the current systems and methods.

SUMMARY

In one embodiment, a system is disclosed for attaching a bump cap to a welding headgear. The system includes a bump cap, and an attachment member. The attachment member is configured to attach the bump cap to a welding headgear.

In another embodiment, a system is disclosed attaching a bump cap to a welding headgear which is attached to a face protection member. The system includes a bump cap, a welding headgear, an attachment member, and a face protection member. The attachment member attaches the bump cap to the welding headgear which is attached to the face protection member.

In still another embodiment, a method of attaching a bump cap is disclosed. The method includes attaching a bump cap to a welding headgear.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
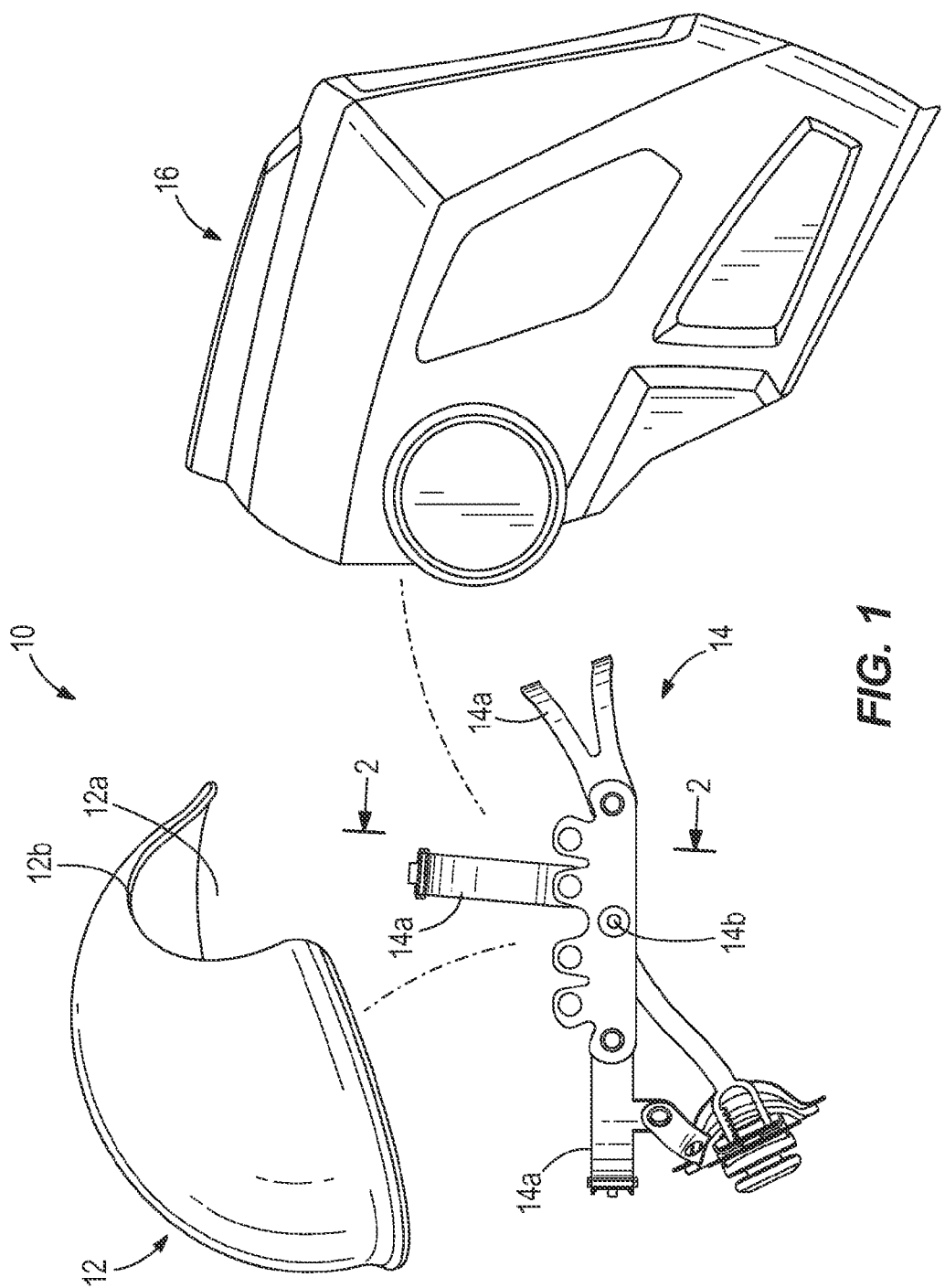
FIG. 1 is a perspective view of one embodiment of a system for attaching a bump cap to a welding headgear attachable to a face protection member.

FIG. 1 is a perspective view of one embodiment of a system 10 for attaching a bump cap 12 to a welding headgear 14 attachable to a face protection member 16. The term "bump cap" is defined as a semi-rigid cap providing limited protection to a user's head from bumps and scrapes in a situation in which head protection is desired but not required under the American National Standards Institute "ANSI." A bump cap does not provide protection equivalent to a hard hat, which is intended for catastrophic or high mass and high energy impacts, but provides protection from bumps and scrapes which a user may be subject to while walking around the welding cell or when accessing hard to reach areas within large weldments. The term "welding headgear" is defined as headgear which attaches to a user's head and which also attaches to a face protection member in order to secure the face protection member to the user's head. The term "face protection member" is defined as a member which provides protection to a user's face during a welding process, such as welding or grinding, in order to protect the user's eyes, face, and neck.

The bump cap 12 has a semi-circular shape and is made of a light-weight material, such as plastic, which covers most, if not all, of the user's head and provides bump and laceration protection. The bump cap 12 comprises a hollow interior 12a and a front cut-out 12b. The welding headgear 14 comprises a plurality of straps 14a which are configured to be disposed over a user's head. The face protection member 16 is pivotally attachable to a pivot point 14b of the welding headgear 14. In the embodiment of FIG. 1, the face protection member 16 comprises a welding helmet. However, in other embodiments, the face protection member 16 may comprise other types of face protection members such as a crown and grinding shield or another type of face protection member.

Figure 2:
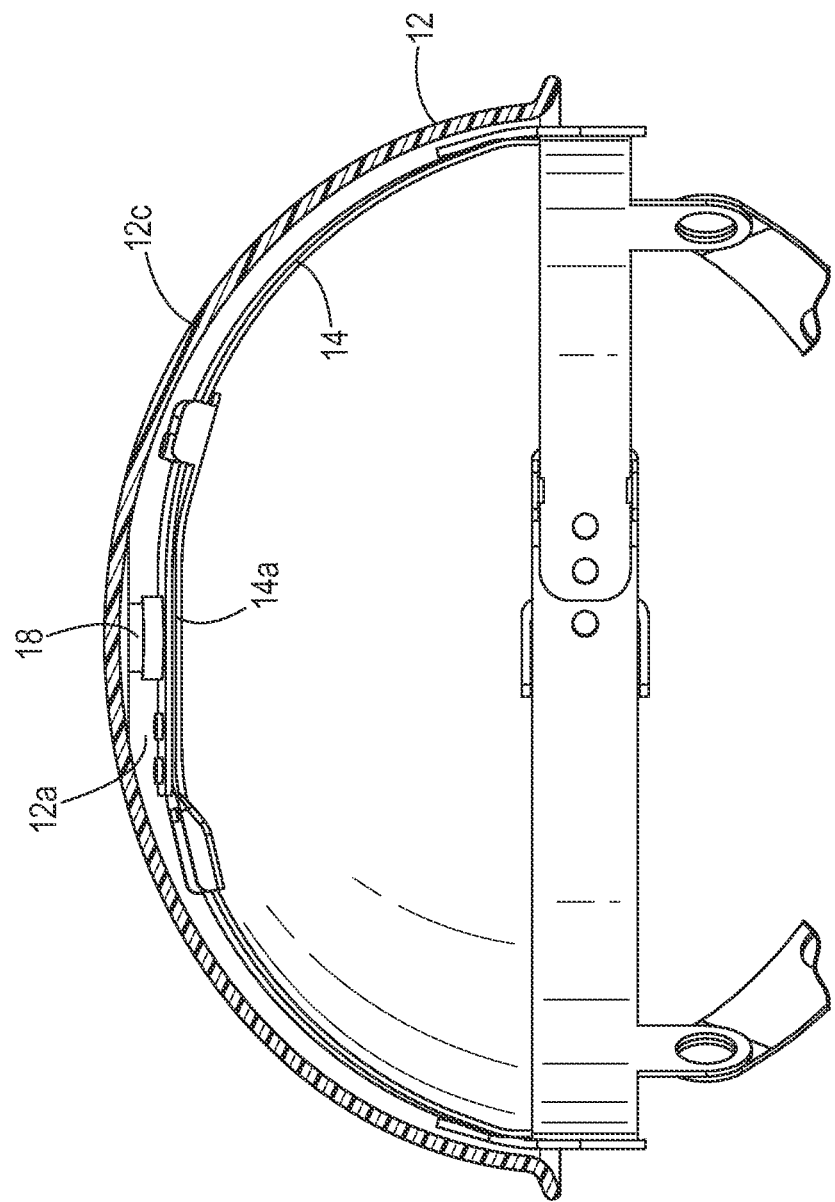
FIG. 2 is a cross-sectional view through line 2-2 of the system of FIG. 1 showing the bump cap disposed over and attached to the welding headgear using an attachment member.

FIG. 2 is a cross-sectional view through line 2-2 of the welding headgear 14 of the system 10 of FIG. 1 showing the bump cap 12 disposed over and attached to the welding headgear 14 using an attachment member 18. The welding headgear 14 is disposed within the hollow interior 12a of the bump cap 12. The attachment member 18 may comprise a snap, a clip, a band, or another type of attachment member for attaching the bump cap 12 to the welding headgear 14. The bump cap 12 may comprise the attachment member 18. The attachment member 18 may be attached to or comprise an inner surface 12c of the bump cap 12. In other embodiments, the attachment member 18 may comprise a separate component than the bump cap 12. The attachment member 18 is attached to at least one of the straps 14a of the welding headgear 14. In other embodiments, the attachment member 18 may attach to various portions of the welding headgear 14.

Figure 3:
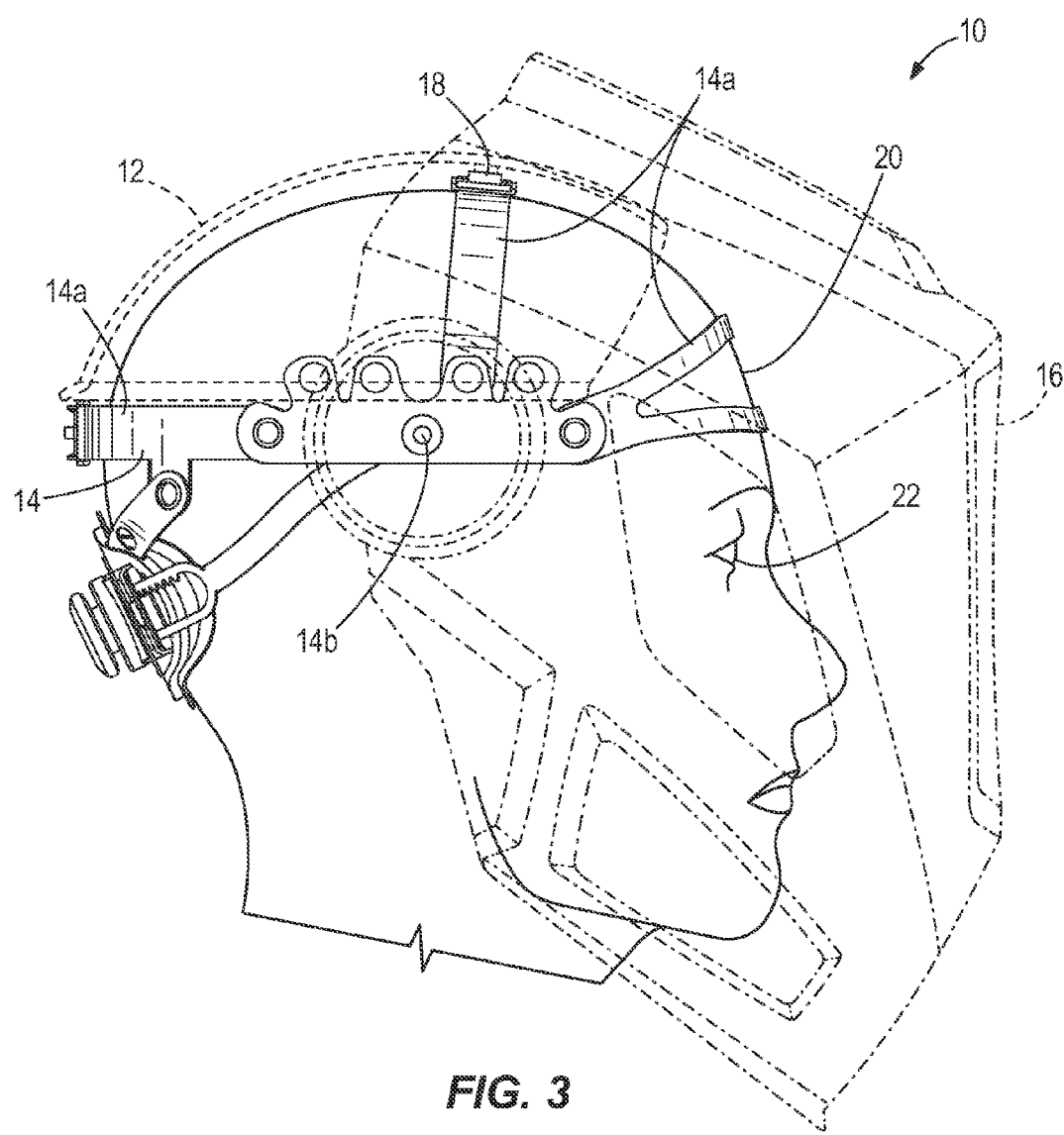
FIG. 3 is a side view of the system of FIG. 1 attached to a user's head with the face protection member disposed in a down position covering a user's eyes.

FIG. 3 is a side view of the system 10 of FIG. 1 attached to a user's head 20 with the face protection member 16 disposed in a down position covering a user's eyes 22. As shown, the straps 14a of the welding headgear 14 are attached to the user's head 20. The bump cap 12 is attached to and over the welding headgear 14 with the attachment member 18. The face protection member 16 is pivotally attached to the pivot point 14b of the welding headgear 14.

It is noted that the bump cap 12 and the face protection member 16 collectively cover an entire top of the user's head 20 when the face protection member 16 is disposed in the down position thereby protecting universal bump protection to the user's head 20.

Figure 4:
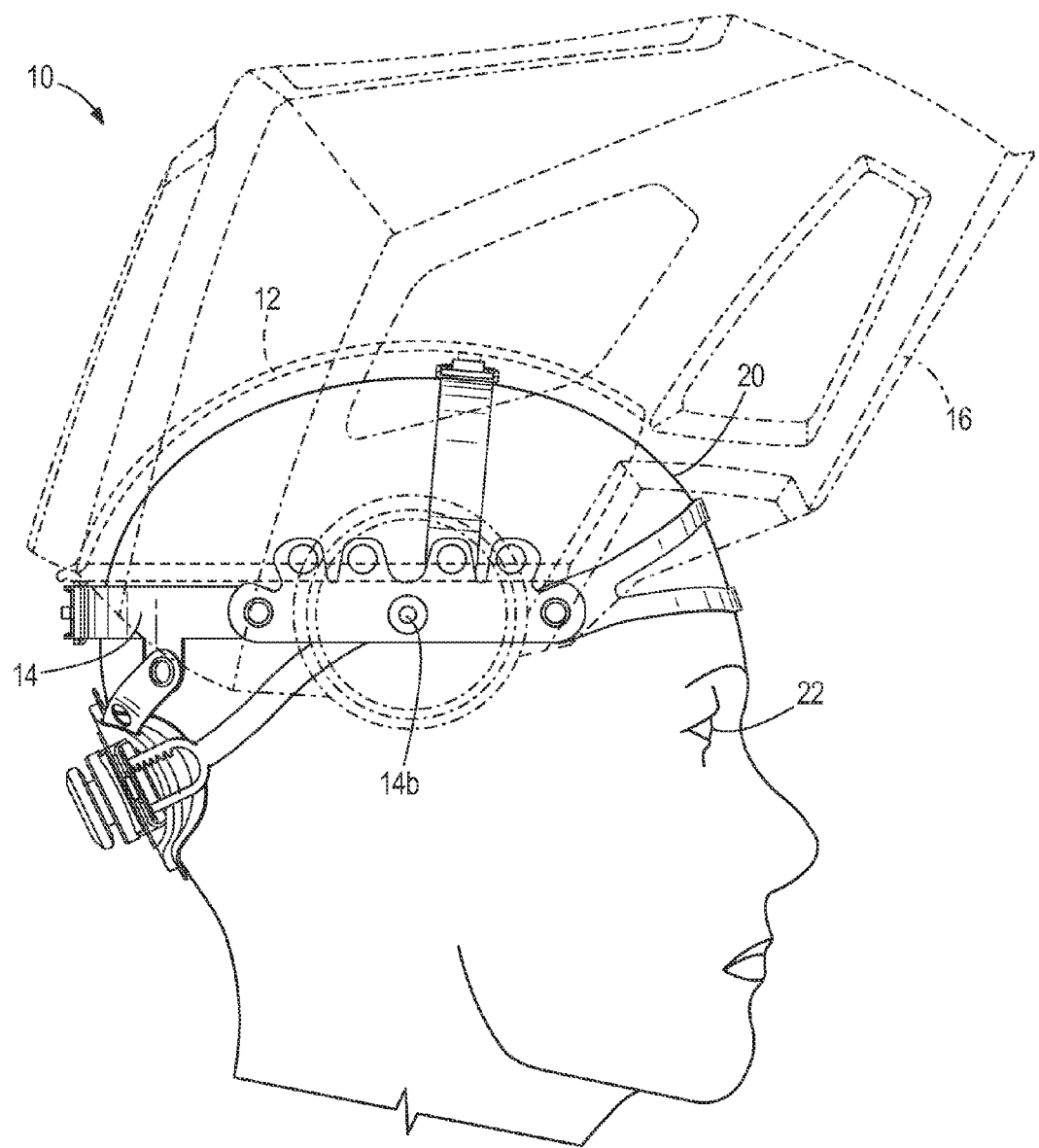
FIG. 4 is a side view of the system of FIG. 3 with the face protection member having been pivotally moved, relative to the welding headgear and the bump cap, to an up position uncovering the user's eyes.

FIG. 4 is a side view of the system 10 of FIG. 3 with the face protection member 16 having been pivotally moved, relative to the welding headgear 14 and the bump cap 12, to an up position uncovering the user's eyes 22. The bump cap 12 does not interfere with the pivoting movement of the face protection member 16. It is noted that the bump cap 12 and the face protection member 16 collectively cover an entire top of the user's head 20 when the face protection member 16 is disposed in the up position as a result of the bump cap 12 and the face protection member 16 overlapping (with the face protection member 16 providing protection to the front of the user's head 20 and the bump cap 12 providing protection to the back and middle of the user's head 20) thereby providing universal bump protection to the user's head 20.

In other embodiments, the system 10 of FIGS. 1-4 may vary. For instance, one or more of the components of the system 10 may be removed or altered, or one or more additional components may be added.

Figure 5:
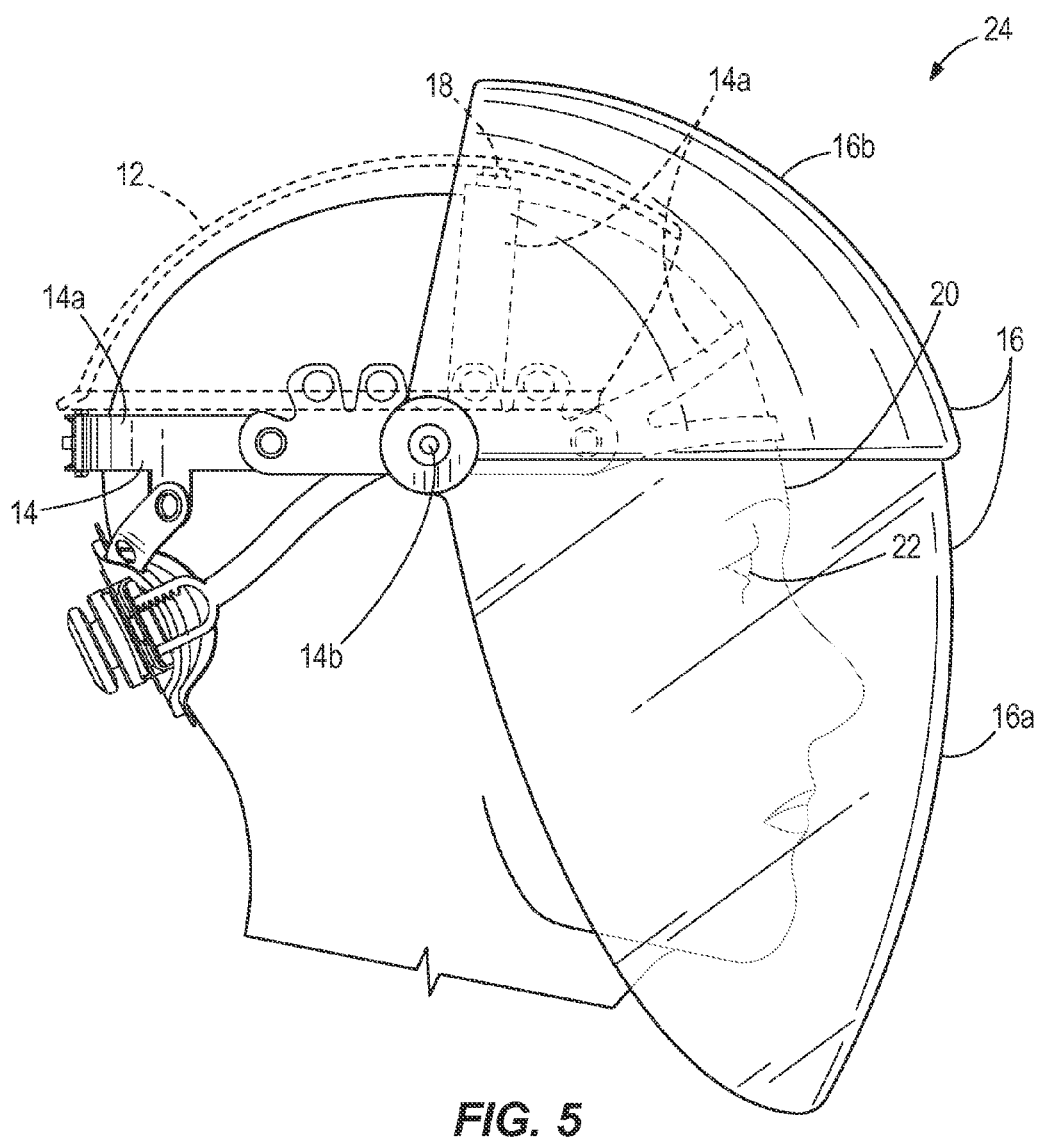
FIG. 5 is a side view of one embodiment of a system attached to a user's head with a face protection member disposed in a down position covering a user's eyes.

FIG. 5 is a side view of one embodiment of a system 24 attached to a user's head 20 with a face protection member 16 disposed in a down position covering a user's eyes. The system 24 of the embodiment of FIG. 5 is identical in all respects to the system 10 of the embodiment of FIGS. 1-4 with the exception that the face protection member 16 comprises a grinding shield 16a attached to a crown 16b with the crown 16b being disposed over and on a front portion of the user's head 20. The grinding shield 16a, attached to the crown 16b, can be used to protect a user's eyes during a welding process comprising grinding. As shown, straps 14a of a welding headgear 14 are attached to the user's head 20. The bump cap 12 is attached to and over the welding headgear 14 with the attachment member 18. The face protection member 16 is pivotally attached to the pivot point 14b of the welding headgear 14. It is noted that the bump cap 12 and the face protection member 16 collectively cover an entire top of the user's head 20 when the face protection member 16 is disposed in the down position thereby protecting universal bump protection to the user's head 20. It is also noted that when the face protection member 16 is pivoted to an up position over the user's head 20 that the bump cap 12 and the face protection member 16 collectively cover an entire top of the user's head 20 as a result of the bump cap 12 and the face protection member 16 overlapping (with the face protection member 16 providing protection to the front of the user's head 20 and the bump cap 12 providing protection to the back and middle of the user's head 20) thereby providing universal bump protection to the user's head 20.

In other embodiments, the system 24 of FIG. 5 may vary. For instance, one or more of the components of the system 24 may be removed or altered, or one or more additional components may be added.

Figure 6:
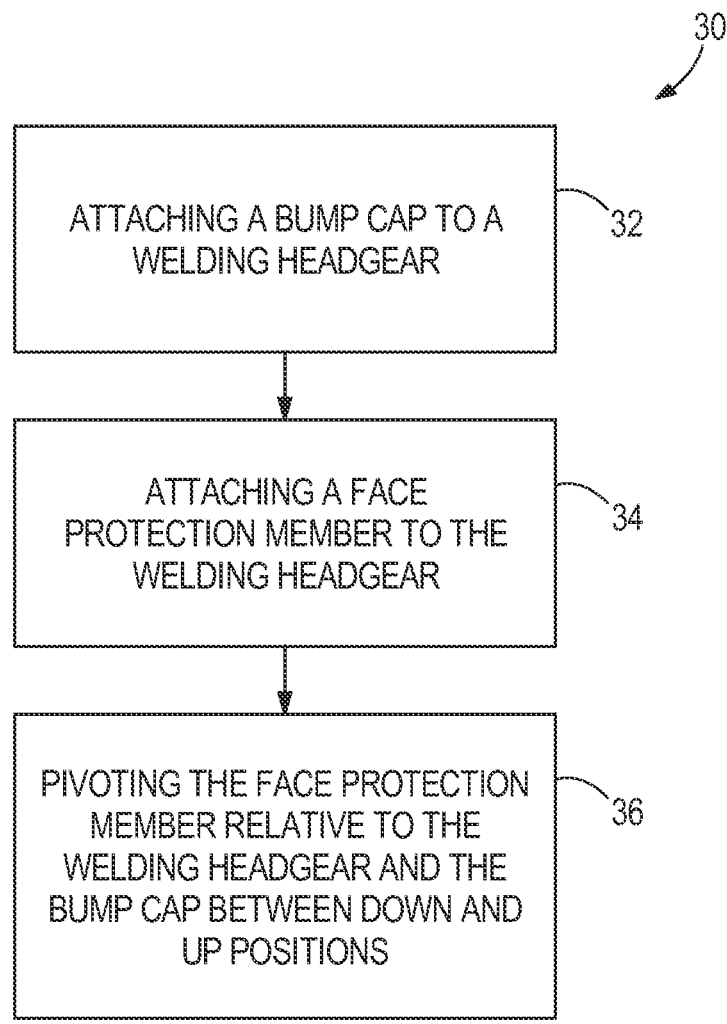
FIG. 6 is a flowchart of one embodiment of a method of attaching a bump cap.

FIG. 6 is a flowchart of one embodiment of a method 30 of attaching a bump cap. The method 30 may utilize any of the systems disclosed herein. In other embodiments, the method 30 may utilize varying systems. In step 32, a bump cap is attached to a welding headgear. In one embodiment, step 32 comprises attaching the bump cap to and over the welding headgear. In one embodiment, step 32 comprises attaching the bump cap to one or more straps of the welding headgear using an attachment member. The attachment member may comprise a snap, a clip, a band, or another type of attachment member for attaching the bump cap to the welding headgear. In step 34, a face protection member is attached to the welding headgear. The face protection member may comprise a welding helmet, a crown and grinding shield, or another type of face protection member. In step 36, the face protection member is pivoted relative to the welding headgear and the bump cap between a down position covering a user's face and an up position uncovering the user's face. It is noted that the bump cap and the face protection member collectively cover an entire top of the user's head both when the face protection member is in the down position and also when the face protection member is in the up position. The method 30 may be used to protect a user's head from bumps during a welding process, such as during welding or grinding. In other embodiments, one or more steps of the method 30 may be altered in order or in substance, one or more steps of the method 30 may not be followed, or one or more additional steps may be added.

One or more embodiments of the disclosure provide significant advantages over one or more of the current options such as: providing head protection against bumps and scrapes for users during a welding process, such as welding or grinding; providing a comfortable and light-weight fit without effecting the fit and feel of a traditional face protection member; protecting welders against a user's face from sparks and spatter similar to that of a weld beanie; or providing other types of advantages.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A system for attaching a bump cap and a face protection member to a welding headgear comprising:
    a bump cap;
    a welding headgear comprising a strap and a pivot point;
    a face protection member directly attachable to the pivot point of the welding headgear to pivot relative to the welding headgear; and
    an attachment member, attached to an inner surface of a top of the bump cap, to attach the bump cap to the strap of the welding headgear;

wherein when the bump cap, the face protection member, and the welding headgear are attached, the face protection member is pivotable, relative to the welding headgear and the bump cap, from a down position for covering a user's face to an up position for uncovering the user's face, and the bump cap is attached to and over the welding headgear with the attachment member.

2. The system of claim 1 wherein the bump cap comprises the attachment member.

3. The system of claim 1 wherein the attachment member comprises a snap, a clip, or a band.

4. A system attaching a bump cap to a welding headgear attached to a face protection member comprising:
   a bump cap;
   a welding headgear comprising a strap and a pivot point;
   an attachment member, attached to an inner surface of a top of the bump cap, attaching the bump cap to the strap of the welding headgear; and
   a face protection member directly attached to the pivot point of the welding headgear and pivotable relative to the welding headgear;
   wherein the bump cap, the face protection member, and the welding headgear are attached to one another with the face protection member being pivotable, relative to the welding headgear and the bump cap, from a down position for covering a user's face to an up position for uncovering the user's face, and the bump cap is attached to and over the welding headgear with the attachment member.

5. The system of claim 4 wherein the bump cap comprises the attachment member.

6. The system of claim 4 wherein the attachment member comprises a snap, a clip, or a band.

7. The system of claim 4 wherein the strap is disposed within a hollow interior of the bump cap.

8. A method of attaching a bump cap and a face protection member to a welding headgear comprising:
   disposing a welding headgear on top of a user's head;
   attaching a bump cap to and over a strap of the welding headgear using an attachment member attached to an inner surface of a top of the bump cap; and
   directly attaching a face protection member to a pivot point of the welding headgear so that the face protection member is pivotable relative to the welding headgear and the bump cap.

9. The method of claim 8 wherein the attaching the bump cap to and over the strap of the welding headgear further comprises disposing the strap on top of a user's head.

10. The method of claim 8 wherein the attachment member comprises a snap, a clip, or a band.

11. The method of claim 8 further comprising pivoting the face protection member relative to the welding headgear and the bump cap between a down position covering a user's face and an up position uncovering the user's face.

* * * * *